United States Patent
Bassi et al.

(10) Patent No.: US 10,520,425 B2
(45) Date of Patent: Dec. 31, 2019

(54) OPTOFLUIDIC DEVICE

(71) Applicants: POLITECNICO DI MILANO, Milan (IT); CONSIGLIO NAZIONALE DELLE RICERCHE, Rome (IT)

(72) Inventors: Andrea Bassi, Milan (IT); Petra Paiè, Milan (IT); Roberto Osellame, Rome (IT); Francesca Bragheri, Rome (IT)

(73) Assignees: POLITECNICO DI MILANO, Milan (IT); CONSIGLIO NAZIONALE DELLE RICERCHE-CNR, Rome (IT)

( * ) Notice: Subject to any disclaimer, the term of this patent is extended or adjusted under 35 U.S.C. 154(b) by 0 days.

(21) Appl. No.: 15/763,742

(22) PCT Filed: Sep. 27, 2016

(86) PCT No.: PCT/EP2016/073007
§ 371 (c)(1),
(2) Date: Mar. 27, 2018

(87) PCT Pub. No.: WO2017/055290
PCT Pub. Date: Apr. 6, 2017

(65) Prior Publication Data
US 2018/0275045 A1 Sep. 27, 2018

(30) Foreign Application Priority Data
Sep. 28, 2015 (IT) .............................. UB2015A3920

(51) Int. Cl.
*G02B 3/12* (2006.01)
*G02B 21/00* (2006.01)
(Continued)

(52) U.S. Cl.
CPC ........ *G01N 21/05* (2013.01); *B01L 3/502707* (2013.01); *B01L 3/502715* (2013.01);
(Continued)

(58) Field of Classification Search
CPC .. G01N 21/05; G01N 15/1434; G01N 15/147; G01N 15/1484; G01N 21/0303;
(Continued)

(56) References Cited

U.S. PATENT DOCUMENTS

| | | | |
|---|---|---|---|
| 7,574,089 B1* | 8/2009 | Zribi | G01N 21/0303 385/122 |
| 8,536,545 B2* | 9/2013 | Wu | G01N 21/6458 250/461.1 |

(Continued)

FOREIGN PATENT DOCUMENTS

DE  102015209418 A1 * 11/2016 ........... G01S 7/4814

OTHER PUBLICATIONS

Bragheri, F. et al. "Optofluidic Chip for Single Cell Trapping and Stretching Fabricated by a Femtosecond Laser" (2010) J. Biophoton. 3(4): 234-243.

(Continued)

*Primary Examiner* — Isiaka O Akanbi
(74) *Attorney, Agent, or Firm* — Volpe and Koenig, P.C.

(57) ABSTRACT

An integrated optofluidic device to illuminate, along an irradiation direction, a fluidic sample containing an object to be analysed, the device comprising: a substrate comprising an entry surface and being made of a material transparent to a light beam incident through the entry surface along the irradiation direction; a microfluidic channel formed in the substrate and having a channel portion intercepting the irradiation direction and extending along a longitudinal axis transverse to the irradiation direction, the microfluidic channel comprising a first flow inlet port for loading a fluidic sample therein, and an elongated lens cavity for an optofluidic cylindrical lens, the cavity being formed in the substrate and being arranged along the beam irradiation direction between the entry surface and the microfluidic channel, (Continued)

wherein the lens cavity is in fluid communication with a lens inlet port for loading a lens fluid.

18 Claims, 9 Drawing Sheets

(51) Int. Cl.
*G01N 21/64* (2006.01)
*G01N 21/05* (2006.01)
*B01L 3/00* (2006.01)
*G01N 21/03* (2006.01)
*G02B 1/06* (2006.01)
*G01N 15/14* (2006.01)

(52) U.S. Cl.
CPC ....... *G01N 15/147* (2013.01); *G01N 15/1434* (2013.01); *G01N 21/0303* (2013.01); *G01N 21/6458* (2013.01); *G02B 1/06* (2013.01); *G02B 3/12* (2013.01); *G02B 21/0076* (2013.01); *G01N 2021/6478* (2013.01); *G01N 2021/6482* (2013.01)

(58) Field of Classification Search
CPC ....... G01N 21/6458; G01N 2021/6482; G01N 2015/144; G01N 2021/0307; G01N 2021/6478; B01L 3/502707; B01L 3/502715; B01L 2300/0654; G02B 1/06; G02B 3/12; G02B 21/0076; G02B 21/16
USPC ........ 356/440, 416, 213, 402, 432, 338, 246
See application file for complete search history.

(56) References Cited

U.S. PATENT DOCUMENTS

| | | | | |
|---|---|---|---|---|
| 8,970,671 B2 * | 3/2015 | Pavani | ................... | G02B 21/16 348/46 |
| 2006/0033987 A1 | 2/2006 | Stelzer | | |
| 2008/0159351 A1 * | 7/2008 | Li | ................. | H01S 3/022 372/53 |
| 2012/0293797 A1 | 11/2012 | Braeckmans | | |
| 2014/0268319 A1 * | 9/2014 | Gulari | ................. | G02B 7/027 359/368 |
| 2018/0120557 A1 * | 5/2018 | Pilard | ................. | G01S 7/4814 |

OTHER PUBLICATIONS

Bruns, T. et al. "Preparation Strategy and Illumination of Three-Dimensional Cell Cultures in Light Sheet-Based Fluorescence Microscopy" (2012) J. Biomedical Optics 17(10): 101518-1-101518-5.
Deschout, H. et al. "On-Chip Light Sheet Illumination Enables Diagnostic Size and Concentration Measurements of Membrane Vesicles in Biofluids" (2014) Nanoscale 6: 1741-1747.
Huisken, J. et al. "Optical Sectioning Deep Inside Live Embryos by Selective Plane Illumination Microscopy" Science 305: 1007-1009.
Huisken, J. and Stalnier, D.Y. "Selective Plane Illumination Microscopy Techniques in Developmental Biology" (2009) Development 136: 1963-1975.
Osellame, R. et al. "Femtosecond Laser Microstructuring: An Enabling Tool for Optofluidic Lab-On-Chips" (2011) Laser & Photonics Reviews 5(3): 442-463.
Paiè, Petra, et al. "Adaptable Acylindrical Microlenses Fabricated by Femtosecond Laser Micromachining" (2015) Frontiers in Ultrafast Optics: Biomedical, Scientific, and Industrial Applications XV. Eds. Helsterkamp et al. Proc. of SPIE 9355: 935516-1 to 935516-7.
Patra, B. et al. "Migration and Vascular Lumen Formation of Endothelial Cells in Cancer Cell Spheroids of Various Sizes" (2014) Biomicrofluidics 8(052109): 052109-1-052109-10.
Rosenauer, M. and Vellekoop, M.J. "Characterization of a Microflow Cytometer with an Integrated Three-Dimensional Optofluidic Lens System" (2010) Biomicrofluidics 4: 043005-1 to 043005-12.
Song, C. et al. "Disposable Flow Cytometer with High Efficiency in Particle Counting and Sizing Using an Optofluidic Lens" (2011) Optics Letters 36(5): 657-659.
Wu, J. et al. "A light Sheet Based High Throughput 3D-imaging Flow Cytometer for Phytoplankton Analysis" Optics Express 21(12): 14474-14480.

* cited by examiner

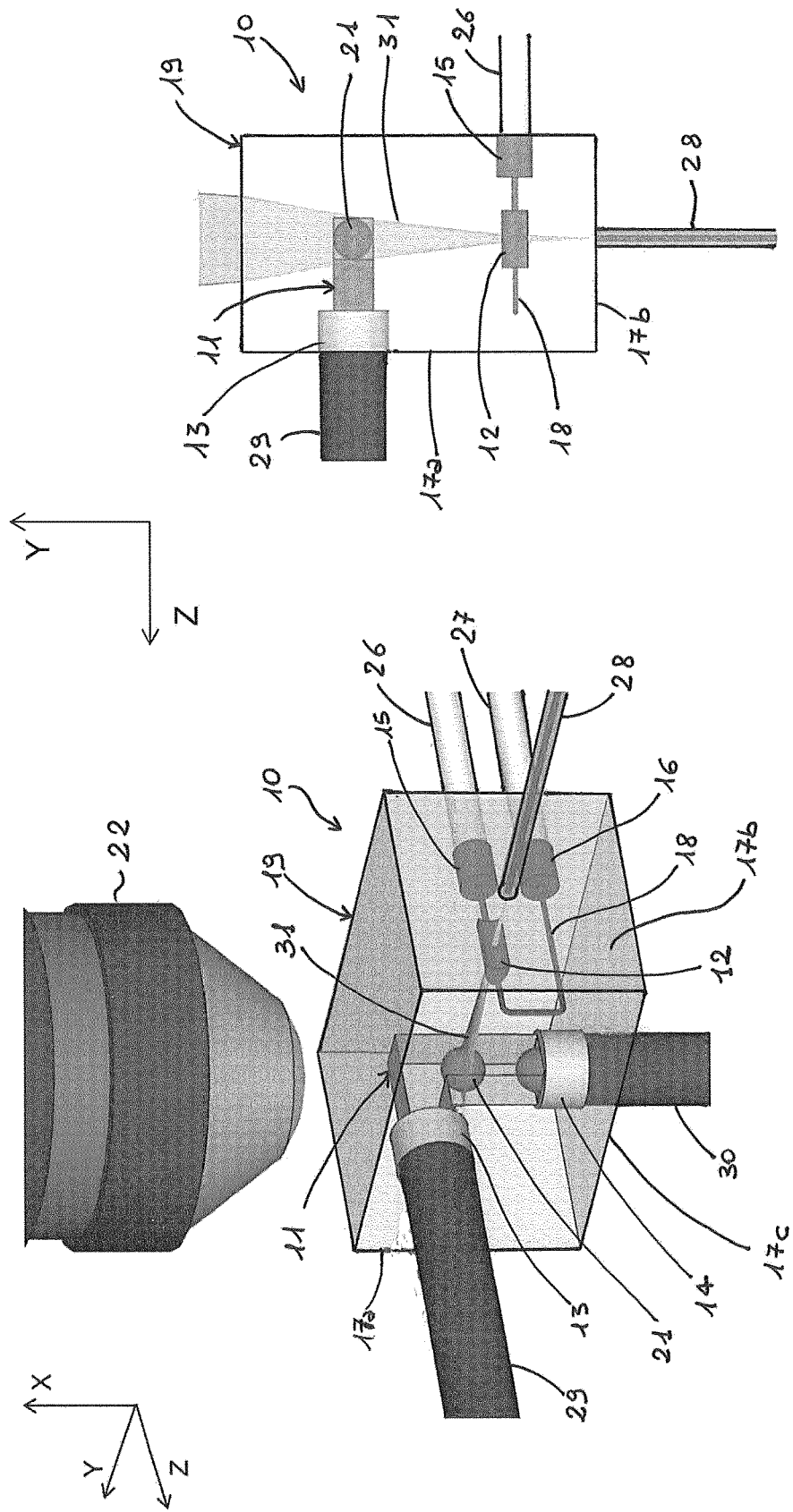

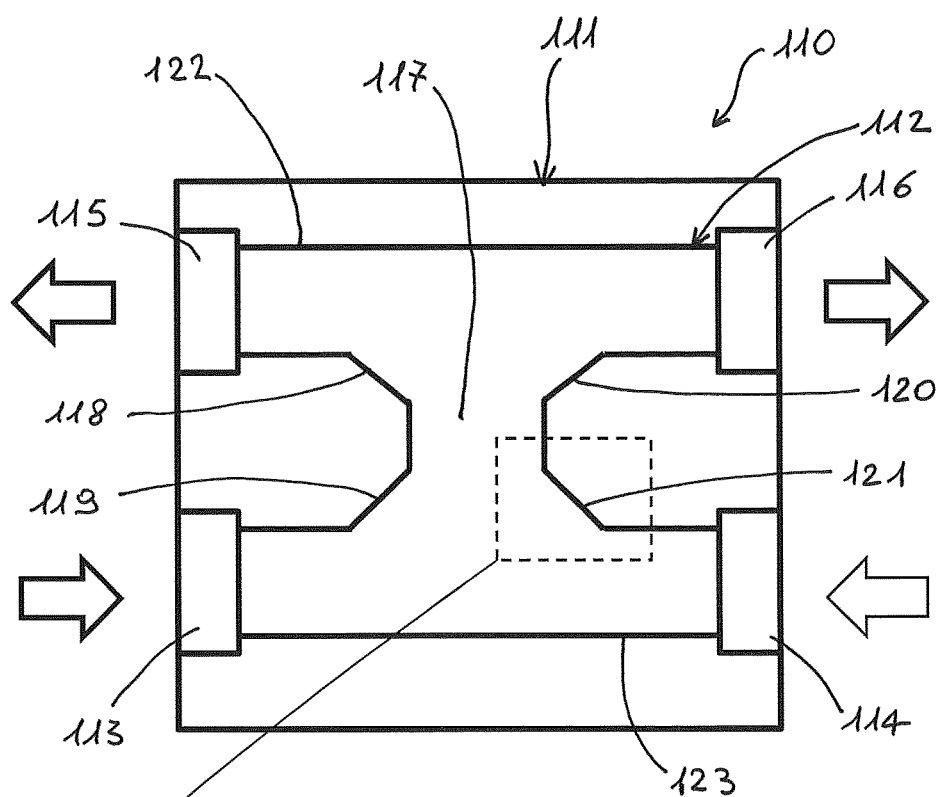
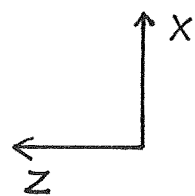
FIG. 11
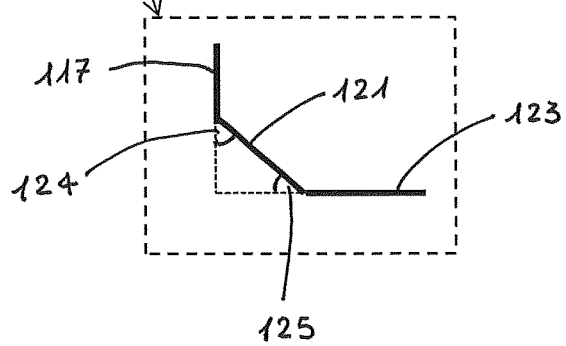
FIG. 11a

OPTOFLUIDIC DEVICE

CROSS REFERENCE TO RELATED APPLICATION

This application is a 35 USC § 371 National Stage application of International Patent Application No. PCT/EP2016/073007, which was filed Sep. 27, 2016, which claims priority to Italian Application No. UB2015A003920, filed Sep. 28, 2015, which is incorporated herein by reference as if fully set forth.

FIELD OF THE INVENTION

The present invention relates to an optofluidic device for irradiating an object in a fluidic sample, in particular for use in light-sheet fluorescence microscopy. The invention concerns also a light-sheet fluorescence microscope and a method for imaging an object in a fluidic sample.

BACKGROUND OF THE INVENTION

Light Sheet Fluorescence microscopy (LSFM) methods, such as Selective Plane Illumination Microscopy (SPIM), have had a big impact on the field of biological imaging since they provide fast, high-resolution optical sectioning over large tissue volumes with low photo-toxicity.

In fluorescence light sheet microscopy, the detection and illumination paths are orthogonal one to another. A sample is illuminated with visible light in a light-sheet volume around the focal plane of the detection optics so that fluorescence is generated only in a thin and well-defined "slice" of the sample.

Deschout H. et al. in "*On-chip light sheet illumination enables diagnostic size and concentration measurements of membrane vesicles in biofluids*", published in Nanoscale, vol. 6(3), pages 1741-7 (2014), discloses a microfluidic chip with integrated waveguide for on-chip light sheet illumination for use in the technique fluorescence single particle tracking.

A review on fluorescence light sheet microscopy is given in "*Selective plane illumination microscopy techniques in developmental biology*" by Huisken, J. and Stainier, D. Y. R., published in Development 136 (12), pages 1963-1975 (2009).

In SPIM, the excitation light is focused by a cylindrical lens to a sheet of light that illuminates only the focal plane of the detection optics, so that no out-of-focus illumination is created (optical sectioning). For a single 2D image, no scanning of the sample is necessary. In SPIM, a stack of images is recorded by moving the sample through the light sheet, usually in a step-wise fashion. The samples, normally embedded in a gel, are imaged individually by mounting them one at a time on a sample holder of a microscope. SPIM was developed to generate multi-dimensional images of samples up to a few millimeters in size. In "*Optical sectioning deep inside live embryos by selective plane illumination microscopy*", in Science 305, pages 1007-1009 (2004) by Huisken J. et al., the sample is embedded in a cylinder of agarose gel. The cylinder is immersed in an aqueous medium that fills the chamber, the excitation light enters the chamber through a thin glass window.

In US 2006/0033987, the object to be studied lies in the two-dimensional object illumination region when an image is recorded, the object being substantially larger than the thickness of this region. A two-dimensional image of the object parts located in this region is recorded by the two-dimensional detector. A three-dimensional image of the object is recorded by scanning the object in the detection direction through the stationary illumination region (or by scanning the illumination region through the object), a two-dimensional image being recorded in each position of the object.

In "*A light sheet based high throughput 3D-imaging flow cytometer for phytoplankton analysis*" by Wu J. et al., published in Optics Express, vol. 21(1:2), pages 14474-80 (2013), the authors report a light sheet fluorescence imaging flow cytometer for 31) sectioning of phytoplankton. The throughput of the instrument is quantified by the sample volume flow rate of 0.5 µl/min with a spatial resolution as achieved by light sheet microscopy.

Bruns T. et al. in "*Preparation strategy and illumination of three-dimensional cell cultures in light sheet-based fluorescence microscopy*", published in Journal of Biomedical Optics, vol. 17(10) 2012, 101518, describes a device for selective plane illumination microscopy (SPIM) of three-dimensional multicellular spheroids, in culture medium under stationary or microfluidic conditions. Cell spheroids are located in a micro-capillary and a light sheet, for illumination, is generated in an optical setup adapted to a conventional inverse microscope. In the illumination device, the optical set-up for beam deflection and focusing, deflection mirror and cylindrical lens, is coupled to the objective turret of the microscope, whereas all other optical and mechanical components are fixed on the base plate of the microscope stage with a customized sample holder. According to the authors, the light sheet and the objective lens can be moved, simultaneously, in the vertical direction and all planes of the spheroid are imaged without re-adjustment of the microscope.

Applicant has observed that in the solution of Bruns T. et al. simultaneous movement of light sheet and objective lens without re-adjustment is possible provided that a pre-calibration of the capillary movement is performed.

A microfluidic device to culture cellular spheroids of controlled sizes and suitable for live cell imaging by selective plane illumination microscopy (SPIM) is described in "*Migration and vascular lumen formation of endothelial cells in cancer cell spheroids of various sizes*" by Patra B. et al., published in Biomicrofluidics, vol. 8(5), 052109 (2014). The spheroid culture chambers are organized in a way such that only a single spheroid is illuminated at a time.

The capability of focusing light in microfluidic channels has attracted much interest in the recent years. This approach is known as optofluidics and describes the combination of optics and microfluidics. Furthermore, the tunability of optofluidic lenses makes them adaptive for a lab-on-a-chip system for biological and chemical analysis.

Paiè P. et al. in "*Adaptable acylindrical microlenses fabricated by femtosecond laser micromachining*", Proc. SPIE 9355, Frontiers in Ultrafast Optics: Biomedical, Scientific, and Industrial Applications XV, 935516 (Mar. 9, 2015) describe an integrated microfluidic cylindrical in-plane lens with optical properties tunable by replacing the liquid used to fill the channel forming the lens. The design of the microlenses was optimised to reduce the effects of spherical aberrations in the focal region. The technique used to realize the device was femtosecond laser micromachining followed by chemical etching, which allows to easily fabricate 3D microfluidic devices with an arbitrary shape.

Osellame R. et al. in "*Femtosecond laser microstructuring: an enabling tool for optofluidic lab-on-chips*", published in Laser & Photonics Reviews, vol. 5, pages 442-463 (2011), offer an overview on the technique of femtosecond laser micromachining.

SUMMARY OF THE INVENTION

Applicant has observed that a mounting procedure of a sample in a gel for 3D imaging is time consuming and often takes much longer than the acquisition itself. Furthermore, such a procedure do not allow imaging of multiple specimens, thereby limiting experimental throughput and statistics.

The present disclosure concerns an integrated optofluidic device for illuminating, along an irradiation direction, a fluidic sample containing an object to be analysed, the device comprising:
- a substrate comprising an entry surface and being made of a material apt to transmit a light beam incident through the entry surface along an irradiation direction;
- a microfluidic channel formed in the substrate and comprising a first flow inlet port for loading a fluidic sample therein, wherein the microfluidic channel comprises a channel portion intercepting the irradiation direction and extending in a longitudinal axis perpendicular to the irradiation direction, and
- an elongated lens cavity for an optofluidic lens extending along a main extension axis transverse to the irradiation direction and defining the lens optical axis, wherein the cavity is formed in the substrate and is arranged in the substrate to intercept the irradiation direction between the entry surface and the microfluidic channel portion, and wherein the lens cavity is in fluid communication with a lens inlet port formed in the substrate for loading a lens fluid.

The microfluidic channel and the lens cavity are formed as hollow structures in the substrate. In some preferred embodiments, the irradiation direction is perpendicular to the entry surface of the substrate.

Preferably, the substrate is a bulk substrate. Preferably, the substrate is made of a material transparent to visible light.

In some preferred embodiments, the substrate is made of glass. Preferably, the substrate is made of silica-based glass.

Preferably, the substrate has planar surfaces. In some embodiments, the substrate has a parallelepiped shape.

Preferably, the microfluidic channel comprises a first flow outlet port, wherein the first flow inlet port and the first flow outlet port define a respective opening on a same surface of the substrate or on different surfaces of the substrate.

Preferably, the elongated lens cavity is filled with a transparent fluid having a refractive index higher or smaller than the refractive index of the transparent material making the substrate so as to form an embedded focusing optical element for a light beam passing through it from an entry surface of the substrate.

Preferably, the elongated lens cavity is configured so as to form a cylindrical lens when filled with a lens fluid of different refractive index from that of the substrate and it is delimited by a curved incidence wall extending along the lens optical axis and a curved exit wall opposite to the light incidence wall and extending along the lens optical axis.

The cylindrical lens is configured to focus the light beam in a plane by forming a light sheet beam passing through the fluidic sample in the channel portion, the light sheet beam being in a plane perpendicular to the longitudinal axis of the channel portion.

In some preferred embodiments, the incidence wall of the lens cavity has a concave shape with respect to the incident light beam while the opposite exit wall has a convex shape, always with respect to the irradiation direction.

Preferably, the microfluidic channel is in fluid connection with a pump circulating system for creating a differential pressure between the first flow inlet port and the first flow outlet port thereby controlling the flow of a fluidic sample through the channel.

Preferably, the microfluidic channel for the fluidic sample has a rectangular or a square cross-section with respect to the flow path. In some embodiments, the cross-sectional area of the microfluidic channel is of from 50×50 to 1000×1000 $\mu m^2$.

In some embodiments, the microfluidic channel has an L-shape.

In some embodiments, the microfluidic channel has a C-shape.

In some embodiments, the optofluidic device further comprises a first flow outlet port, a second flow inlet port and a second flow outlet port, wherein
- the microfluidic channel has an H-shape and comprises a lower channel branch, an upper channel branch extending in a direction substantially parallel to the lower channel branch and a connecting channel portion transverse to the upper and lower channel branches and opening into them, the connecting channel portion corresponding to the channel portion intercepting the irradiation direction, and
- the connecting channel portion extends along a main axis perpendicular to the irradiation direction.

Preferably, in a H-shaped microfluidic channel, the first inlet port and the first outlet port define a respective opening on a respective surface of the substrate or on a substrate surface being the same for the first inlet port and the first outlet port for circulating a flow of the fluidic sample from the first flow inlet port to the first outlet port. The second inlet port and the second outlet port define a respective opening on a respective surface of the substrate or on a substrate surface being the same for the second inlet port and the second outlet port for circulating a buffer fluidic stream from the second flow inlet port to the second outlet port, so that the flow of the fluidic sample and the flow of the buffer fluidic stream merge in the connecting channel portion.

Preferably, the upper channel branch of the H-shaped channel extends from the first outlet port to the second outlet port and the lower channel branch extends from the first inlet port to the second inlet port.

Preferably, the first inlet port and the first outlet port of the H-shaped microfluidic channel are fluidly connected with a first flow circulating system to flow a fluidic sample through the channel portion and the second inlet port and the second outlet port are fluidly connected with a second flow circulating system to flow a buffer stream through the channel portion.

The optofluidic device in accordance with the present disclosure allows continuous sample delivery in a microfluidic channel and continuous optical sectioning by only controlling the stream of the fluidic sample through the channel, in particular without the need of moving the sample by means of external translation parts or of manually positioning the sample during measurements. In some embodiments, the device makes possible a continuous flow of the object under study without it touching the channel walls, which may induce an object's rotation. Three-dimensional reconstruction of the entire volume of the scanned object can be performed by using image processing procedures known per se.

In some embodiments, the object to be analysed can be a single cell, a cell aggregate, a microtissue, a spheroid, an organoid, an embryo (e.g. *Drosophila* or *zebrafish*), or a sub-millimetre biopsy. In some embodiments, the object has a diameter of from 10 µm to 2 mm.

The present disclosure also provides for a microscope according to claim 16.

The present disclosure relates also a method in accordance to claim 17.

BRIEF DESCRIPTION OF THE DRAWINGS

The present invention will now be described in more detail hereinafter with reference to the accompanying drawings, in which some, but not all embodiments of the invention are shown. Drawings illustrating the embodiments are not-to-scale schematic representations.

FIG. 1b is a cross-sectional view of the device of FIG. 1a.

FIG. 2a is a perspective view of the device of figures FIG. 1a when in use for light-sheet fluorescence microscopy.

FIG. 2b is a top plan view of the device of FIG. 2a.

FIG. 3b is a cross-sectional view of the device of FIG. 3a.

FIG. 11 shows a cross-sectional view of an optofluidic device according to a further embodiment of the invention.

FIG. 11a is an enlargement of inset from FIG. 11 (indicated by a dashed line) to show more clearly some details.

DETAILED DESCRIPTION

Figure 1A:
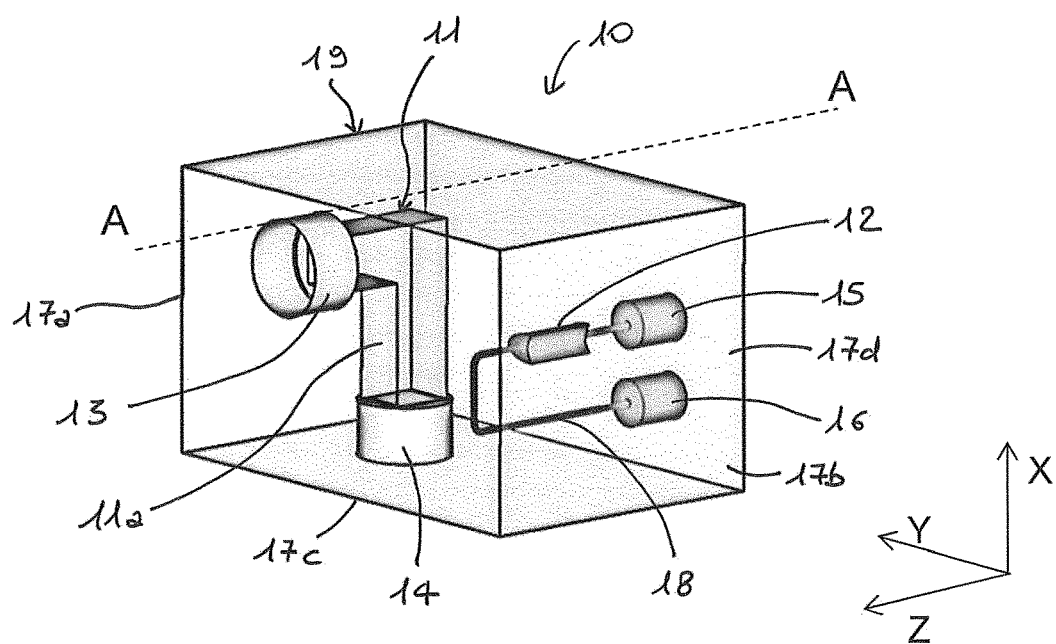
FIG. 1a is a perspective view of an integrated optofluidic device according to a first embodiment of the invention.
Figure 1B:
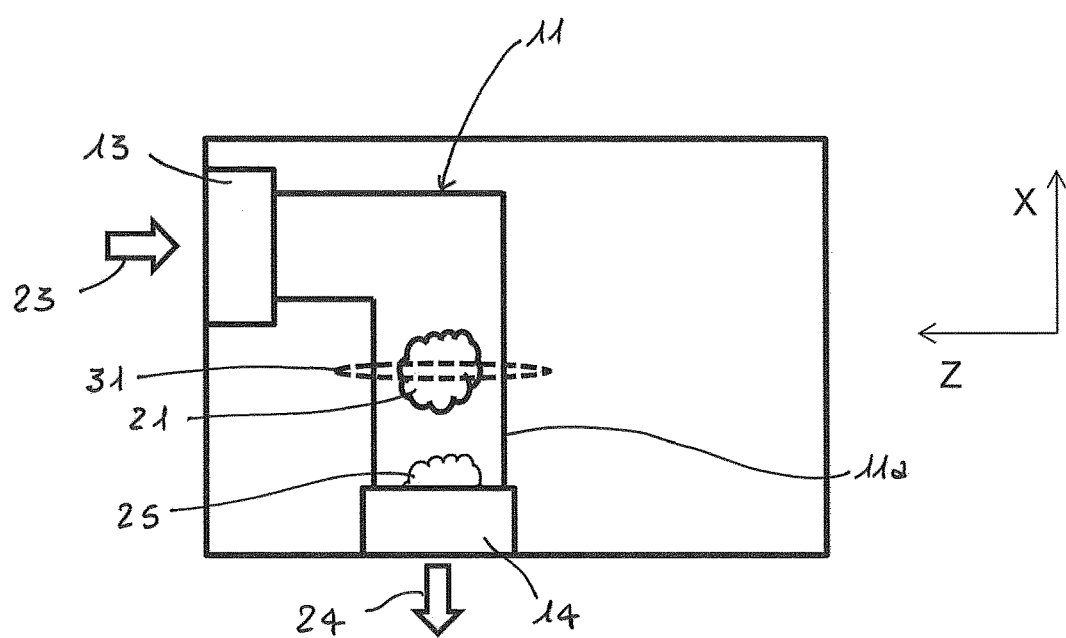

FIG. 1a is a perspective view of an integrated optofluidic device according to a first embodiment of the invention. FIG. 1b is a cross-sectional view of the device of FIG. 1a taken along the plane XZ of line AA shown in FIG. 1a. An optofluidic device 10 comprises a substrate 19 made of a material transparent to light, preferably to visible light and in the near infrared wavelength region. In some preferred embodiments, the substrate is glass, for example fused silica. The substrate of the device of FIGS. 1a and 1b has a rectangular or square parallelepiped shape. A microfluidic channel 11 is formed in substrate 19 as a hollow structure inside the bulk material of the substrate. The channel 11 has an L-shape and comprises an inlet port 13 defining an opening on a first surface 17a of the substrate. The microfluidic channel further comprises a flow outlet port 14 defining an opening on a second surface 17c of the substrate 19, the second surface 17c being adjacent to the first surface 17a. In the embodiment shown in the figure, the microfluidic channel 11 comprises two straight channel portions, substantially perpendicular one to another. When in use, a fluidic sample containing at least an object to be analysed is loaded from flow inlet port 13 and circulates through the channel to the flow outlet port 14, from which it exits. Preferably, the L-shaped channel 11 has flow path between the inlet and the outlet port of square or rectangular cross-section. In some embodiments, cross-sectional area is of from 50×50 to 1000×1000 µm². It is to be understood that the flow direction shown in the figure, and in general in the present detailed description, from inlet to outlet can be inverted. For example, in FIGS. 1a and 1b, the fluidic sample can enter from 14 and exit from 13.

The device 10 further comprises an elongated lens cavity 12 for an optofluidic lens, the cavity being formed in the substrate 19 and being spaced from the microfluidic channel 11.

The lens cavity is to be filled with a fluid having a refractive index higher or smaller than the refractive index of the glass making the substrate so as to form an embedded focusing optical element for a light beam passing through it from an entry surface of the substrate.

The microfluidic lens and thus the lens cavity 12 is arranged with respect to the microfluidic channel 11 such that a beam irradiating the fluidic sample flowing in the channel enters the substrate and passes through the lens before traversing the sample. In the present embodiment and as explained more in detail with reference to FIGS. 2a and 2b, an optical beam enters the substrate 19 along a beam irradiation direction (Y-axis) from a substrate entry surface 17b, passes through the lens 12 and then through a channel portion 11a between the flow inlet and outlet ports of the microfluidic channel 11. In the embodiments of FIGS. 1a to 2b, the irradiation direction of the light beam is perpendicular to the entry surface 17b.

The channel portion 11a extends along a longitudinal axis (X-axis) it is preferably a straight portion.

The lens cavity is elongated in the direction of a main axis, defining the lens optical axis, which is transverse and preferably perpendicular to the irradiation direction. The elongated lens cavity is delimited by a curved incidence wall extending along the lens optical axis and a curved exit wall opposite to the incidence wall and extending along the lens optical axis.

When filled by a fluid, the curved incidence wall of the cavity forms a light incidence surface (incident refractive index interface) of the lens and the curved exit wall forms a light exit surface of the lens (exiting refractive index interface). Preferably, the lens optical axis extends along an axis (Z-axis), which is perpendicular both to the longitudinal axis of the channel portion 11a and to the irradiation direction.

The lens cavity is configured so as to form a cylindrical lens when filled with a lens fluid of different refractive index from the substrate.

Preferably, the incidence wall of the lens cavity has a circular-arc cross section taken in plane perpendicular to the lens optical axis. The circular-arc cross section of the incidence wall has a first radius.

In some embodiments the exit wall of the lens cavity has a circular-arc cross section (taken in plane perpendicular to the lens optical axis) having a second radius different from the first radius of the circular arc of the incidence wall. In these embodiments and most generally, the radius of the circular arc of the exit wall can also be infinite, i.e. the exit wall forms a planar surface of the lens, whereas the radius of the circular arc of the light incidence wall is represented by a finite number. In case of planar wall, the incidence wall has preferably a convex shape with respect to the irradiation direction so as to form, when filled with a fluid, a plano-convex cylindrical lens.

In some other embodiments, the elongated lens cavity has an aspherical wall to reduce optical aberrations caused by the glass/fluid interface. The term "aspherical" is used herein in the sense that the wall cross-section in planes transverse to its optical axis is not circular, for example it is parabolic or more generally a curve described by a polynomial function.

Preferably, the incidence wall has a circular-arc cross section since it is preferred that the incoming light beam crosses perpendicularly the first refractive index interface formed by the lens. Preferably, when the incidence wall has a circular-arc cross section, the exit wall has an aspherical surface profile.

Shape of the elongated lens can be optimised to reduce the effects of spherical aberrations, taking advantage of the FLM technique, as described in previously cited publication by Paiè P. et al. (2015).

In some embodiments, the incidence wall of the lens cavity has a concave shape with respect to the irradiation direction of the beam while the opposite exit wall has a convex shape, always with respect to the irradiation direction. In these embodiments, the cylindrical lens has a convex-concave shape. Preferably, the convex-concave cylindrical lens has an aspherical wall. Preferably, the wall with an aspherical surface profile is the exit wall of the lens cavity, i.e. the exit refractive index interface of the lens.

The lens cavity and thus the optofluidic lens when filled with a fluid having a different refractive index from that of the substrate is configured so as to focus a light beam to a sheet of light in a plane, also referred to the light-sheet plane (ZY in the figure), comprising the irradiation direction. The elongated lens is arranged in the substrate with its main axis (lens optical axis) perpendicular to the impinging beam direction (Z-axis).

The lens cavity has a first end and a second end, the first and the second end being connected, respectively, with a lens inlet port 15 and a lens outlet port 16 for loading and unloading, from the respective lens cavity ends, the lens fluid. In the embodiments shown in the figures, connection of the lens cavity with the lens inlet port and the lens outlet is through a loading/unloading channel 18 (hollow when empty) formed in the substrate 19 and connected to both the first and the second ends of the lens cavity. The lens inlet port and the lens outlet port define a respective opening on a surface 17d of the substrate. In the embodiment of FIGS. 1a and 1b, surface 17d is opposite to surface 17a having the opening for the flow inlet port for the fluidic sample. It is to be understood that lens inlet and outlet ports can be formed on different surfaces of the substrate 19, for example surface 17a or 17b. It is also envisaged that lens inlet opens on a surface different from the surface of the opening of the lens outlet.

The L-shaped channel 11 is configured to have the channel portion 11a extending perpendicularly to the light-sheet plane. In this way, when a fluidic sample flows in the channel portion, the flow path of the sample from the inlet port to the outlet port is perpendicular to the light-sheet beam (X-axis in FIGS. 1a and 1b). Arrows 23 and 24 indicate the flow direction, in and out, respectively, of the fluidic sample through channel 11 (FIG. 1b). Fluidic sample comprises an object 21 to be analysed by the light-sheet beam. The object can be a single cell, a cell aggregate, a microtissue, a spheroid, an organoid, an embryo (e.g. *Drosophila* or *zebrafish*), or a sub-millimetre biopsy. In some embodiments, the object has a diameter of from 10 µm to 2 mm. One or more objects are dispersed in a fluid that transports the objects through the channel. For example, FIG. 1b shows a second object 25, which has already passed through the imaging beam, and it is close to the outlet port of the channel. The fluid containing the objects can be, for example, a water solution, a saline solution, blood plasma or cell culture media. In the present description and claims, the fluid together with the object(s) contained in the fluid is referred to as fluidic sample.

The microchannel and the lens cavity are advantageously formed by femtosecond laser micromachining (FLM) of a bulk glass block, a technology that allows hard material processing at high level of precision and control. As per se known, subsequent to permanent material modification due to nonlinear absorption of focused femtosecond laser pulses, chemical etching is carried out to form hollow structures in the bulk material. FLM can create complex 3D microfluidic networks in bulk glass with high quality surfaces (e.g. with surface roughness as low as 10 nm). For silica-based glass substrates, chemical etching can be realized by immersing the processed glass in a hydrofluoric acid (HF) solution. Details of a FLM process suitable for producing a lens cavity with acylindrical profile is described in previously cited publication of Pale P. et al. in Proc. SPIE 2015.

FLM technique can be used also to create access holes forming flow inlet and outlet ports 13, 14, 15 and 16 on the side walls 17a, 17b and 17d of the glass substrate 19 in order to achieve easy connection with external capillary tubes (not shown in FIGS. 1a and 1b) for in-flow and out-flow.

FIGS. 2a and 2b show the device of figures FIGS. 1a and 1b when in use for light-sheet microscopy. In particular, FIG. 2a is a perspective view of the optofluidic device 10 showing some further details on the loading and unloading of the fluidic sample and of the lens fluid for the cylindrical lens, whereas FIG. 2b is a top plan view of the assembly of FIG. 2a. Same referral numbers indicate same elements described with reference to FIGS. 1a and 1b.

The lens cavity 12 is filled with a fluid as optical medium with a different refractive index from that of the substrate 19 thereby obtaining an optofluidic lens embedded in the substrate. The fluid filling the lens cavity is referred in the present description and claims to as lens fluid. Lens inlet port 15 and lens outlet port 16 connected to the lens cavity 12 through loading/unloading channel 18 are formed as access holes on a surface of the substrate. A first and a second lens tube 26 and 27 (only partly shown), external to the device, are connected, respectively, to lens inlet and outlet port 15, 16. Lens tubes are in fluid connection with a pump system (not shown) for loading and unloading the lens fluid in the lens cavity. In an embodiment, the pump system comprises an external microfluidic syringe pump, which can be connected with the lens inlet port for fluid injection.

An optical fibre 28 transmits a light beam along an irradiation direction (Y axis) to the optofluidic cylindrical lens 12 which creates the light sheet beam 31. In an embodiment, after alignment procedures, the optical fibre 28 is attached to the entry surface 17b of substrate 19 at a surface position such that the beam emitted from the fibre intercepts the optofluidic lens. Preferably, the optical fibre is attached to the substrate so as the light beam is substantially perpendicular to the entry surface of the transparent substrate. In an embodiment (not shown), an access hole is formed on the entry surface 17b for fibre attachment and the fibre is fixed in the hole after optical alignment.

The delivery of the fluidic sample containing object 21 to the channel portion 11a illuminated by light sheet beam 31 is realised by fluidly connecting the microfluidic channel to an external fluidic delivery circuit (only partly shown), which guarantees a controlled flow through the channel. The sample fluidic circuit comprises a first and second tubes 29 and 30 (only partly shown), which are connected, respectively, to the flow inlet port 13 and to flow outlet port 14. Flow inlet and outlet ports are configured as access holes opening to the surfaces 17a and 17c of the substrate 19. In some embodiments, access holes have a diameter larger than the cross-section of the branches of the microfluidic channel so as to engage the outer surface of the external tubes.

The diameter of each access hole for insertion/outputting of the lens fluid or of the sample is designed, preferably by FLM, to match the outer diameter of the respective tube. The tubes can be inserted in the access holes by using a translation stage. Once an end of a tube is firmly inserted in the access hole, it is fixed into the hole. For example, tubes are glued to the inlets and outlets by means of UV-curable resin.

The free ends of tubes 29 and 30 (opposite to those connected to the inlet and outlet ports, not shown) are inserted into respective cuvettes filled with the fluidic sample, thus acting as inlet and outlet reservoirs for the fluidic sample (external to the device and not shown in the figures). In an embodiment, a controlled microfluidic flow is obtained by creating a differential pressure between the two reservoirs by a commercial pump system (not shown).

In particular, by unbalancing the pneumatic pressure at the inlet and the outlet of the channel, the liquid starts to move in the channel and an automatic flow of the fluidic sample is achieved by controlling the pressure of the inlet and outlet reservoir. In an embodiment, the pump system has two pressure-driven pumps, each pump being in fluid connection with a respective reservoir. The pumps apply different pressures at the input and at output reservoirs so as to control the flow start and flow rate of the fluidic sample through the channel 11. In this way, since the fluid of the fluidic sample transports the object, object movement along the channel is controlled. In another embodiment, one or more syringe pumps can be used for fluid flow. Although active control of the flow of the fluidic sample in the channel is preferred in some embodiments, passive microfluidic pumping using capillary pressure can be envisaged.

In order to show the illumination and detection arrangements, FIG. 2a shows a microscope objective lens 22 for collecting the fluorescence light emitted from the sample. To improve clarity, the objective lens is not shown in FIG. 2b. The objective lens 22 is arranged such that its optical axis, which defines a detection direction, is substantially perpendicular to the plane of light sheet 31 penetrating the sample. In this way, the detection direction (X axis) is parallel to the channel portion 11a. The microscope objective lens is optically coupled to a 2D photodetector device (not shown), usually an image sensor, for acquisition of the image of the plane of illumination.

In some embodiments, with the term "perpendicular" between the detection and irradiation directions and between the irradiation direction and the flow path along the microfluidic channel it is meant an orthogonality within 0.5 degrees of tolerance.

In some embodiments, with the term "perpendicular" between the lens optical axis and the irradiation direction it is meant an orthogonality within 0.5 degrees of tolerance.

During sample flow along a direction perpendicular to the light sheet plane (i.e. moving along the channel portion 11a), the object 21 is optically sectioned. In particular, an image is acquired as single 2D slice and an axial stack of 2D slices are recorded by the photodetector device.

The presently disclosed device allows a continuous movement of the object through the light sheet plane and an automatic and accurate optical alignment of the lens and thus of the light sheet beam with the object of the fluidic sample. In an embodiment, scanning of the object is performed by flowing the sample at a constant speed through the light sheet.

Figure 3A:
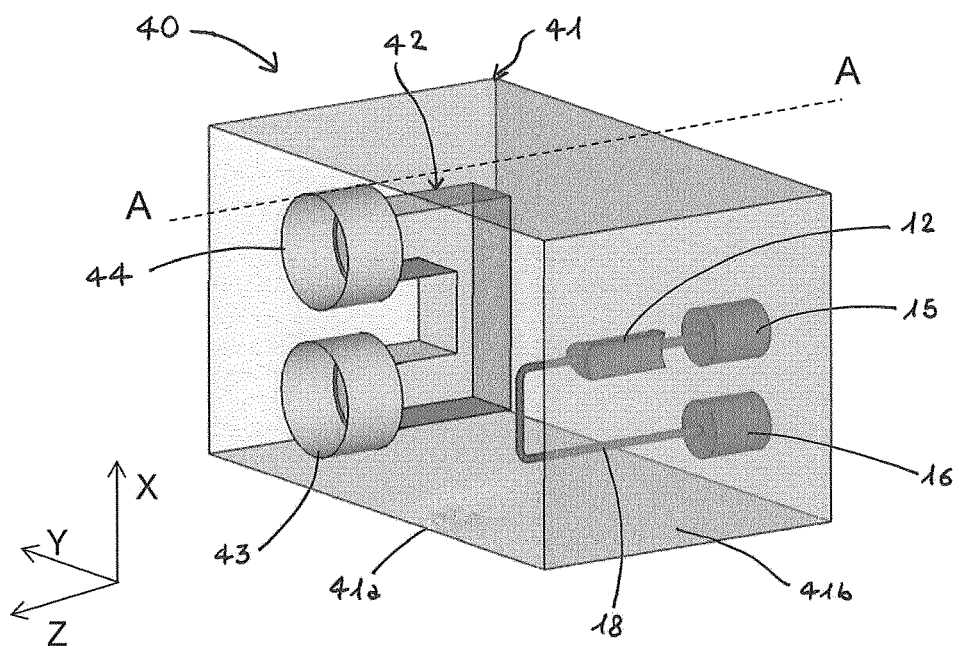
FIG. 3a is a perspective view of an integrated optofluidic device according to a second embodiment of the invention.
Figure 3B:
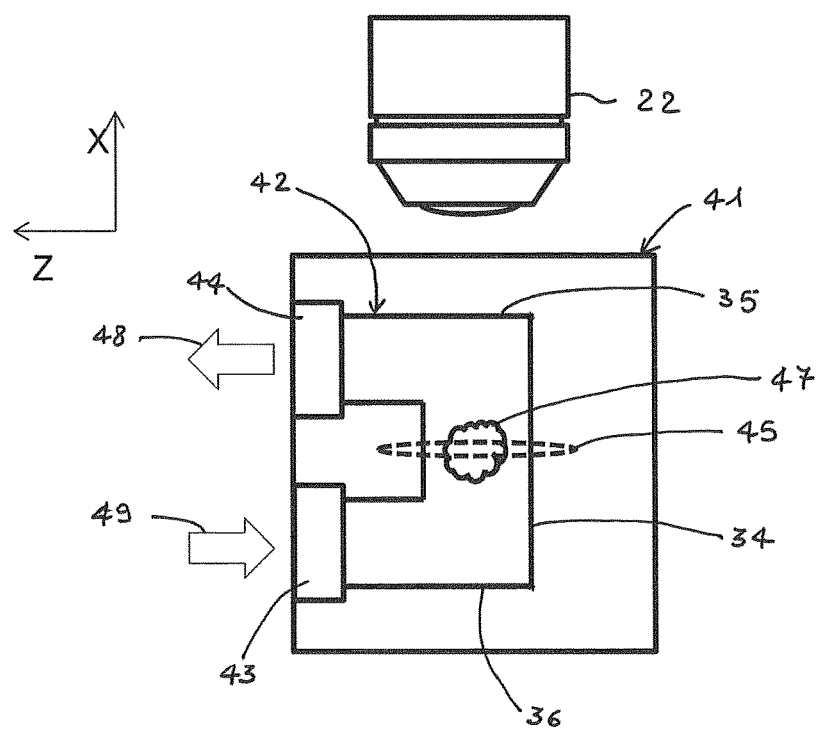

FIG. 3a is a perspective view of an integrated optofluidic device according to a second embodiment of the invention. FIG. 3b is a cross-sectional view of the device of FIG. 3a taken along the plane XZ of line AA shown in FIG. 3a. A main difference with respect to the device of the first embodiment is the shape of the microfluidic channel for the fluidic sample. In the present embodiment, the channel is C-shaped. The C-shape allows a flow of the sample perpendicular to the optical axis of the optofluidic cylindrical lens and thus to the light sheet beam.

With a C-shaped channel configuration and according to some embodiments, the optofluidic device can be illuminated from the bottom (i.e. light entering from a bottom surface of the substrate) in transmission mode to achieve brightfield imaging of the sample in a standard commercial up-right microscope. Alternatively, the optofluidic device can be illuminated from the top to achieve brightfield contrast in a commercial inverted microscope.

In FIGS. 3a and 3b, an optofluidic device 40 comprises a substrate 41 made of a material transparent to a light beam, preferably glass. A C-shaped microfluidic channel 42 is formed in substrate 41 as a hollow structure inside the bulk material of the substrate. The channel 42 comprises a flow inlet port 43 defining an opening on a first surface 41a of the substrate.

The microfluidic channel further comprises a flow outlet port 44 defining an opening preferably on the same surface 41a of the substrate. When in use, a fluidic sample containing at least an object 47 to be analysed (shown in FIG. 3b) is loaded from flow inlet port 43 and circulates through the channel to the flow outlet port 44, from which it exits, as indicated by arrows 48 and 49 in FIG. 3b.

The C-shaped channel 42 comprises an intermediate channel portion 34 between an upper channel portion 35 and a lower channel portion 36. The lower channel portion 36 and the upper channel portion 35 end, respectively, with the flow inlet port 43 and flow outlet port 44. The C-shaped channel is arranged in the substrate so as the intermediate channel portion 34 is arranged vertically between horizontal upper and lower channel portions 35, 36 and extends perpendicularly to the irradiation direction (Y axis) of a light beam entering the substrate from entry surface 41b.

In the embodiment shown in FIGS. 3a and 3b, portions of the channel forming the C-shape are straight sections. In some embodiments (as that shown in FIGS. 3a and 3b), the C-shaped channel 42 has a flow path between the inlet and the outlet ports 43 and 44 of square or rectangular cross-section, although cross-sectional shape should not be considered limitative.

Optofluidic lens and microfluidic arrangements in the substrate for loading and unloading the lens fluid are the same as those described with reference to FIGS. 1a to 2b, same reference numbers corresponding to same elements and details are herein omitted.

Elongated lens cavity 12 is arranged in the substrate 41 with its main extension axis (i.e. optical axis of the cylindrical lens) along a direction transverse to the intermediate channel portion 34 and preferably perpendicular to it. Preferably, the lens optical axis is perpendicular to the irradiation direction and to the longitudinal axis of the channel portion 34. A light beam enters the substrate 41, from entry surface 41b, along an irradiation direction, passes through the optofluidic cylindrical lens 12 to be converted into a light sheet beam 45, which illuminates a plane crossing the intermediate portion 34 of microfluidic channel 42. In the embodiment shown in the figures, the irradiation direction is perpendicular to the entry surface 41b of substrate 41. A fluidic sample containing object 47 (indicated in FIG. 3b) flows through the light sheet plane. An objective lens 22 positioned with its optical axis along the direction of flow of the sample and orthogonal to the light sheet beam collects the fluorescence light emitted from the object.

When in use, a fluidic sample containing at least an object 47 to be analysed is loaded from flow inlet port 43 and circulates through the channel to the flow outlet port 44, from which it exits, as indicated by arrows 49 (in) and 48 (out) in FIG. 3b.

Figure 4:
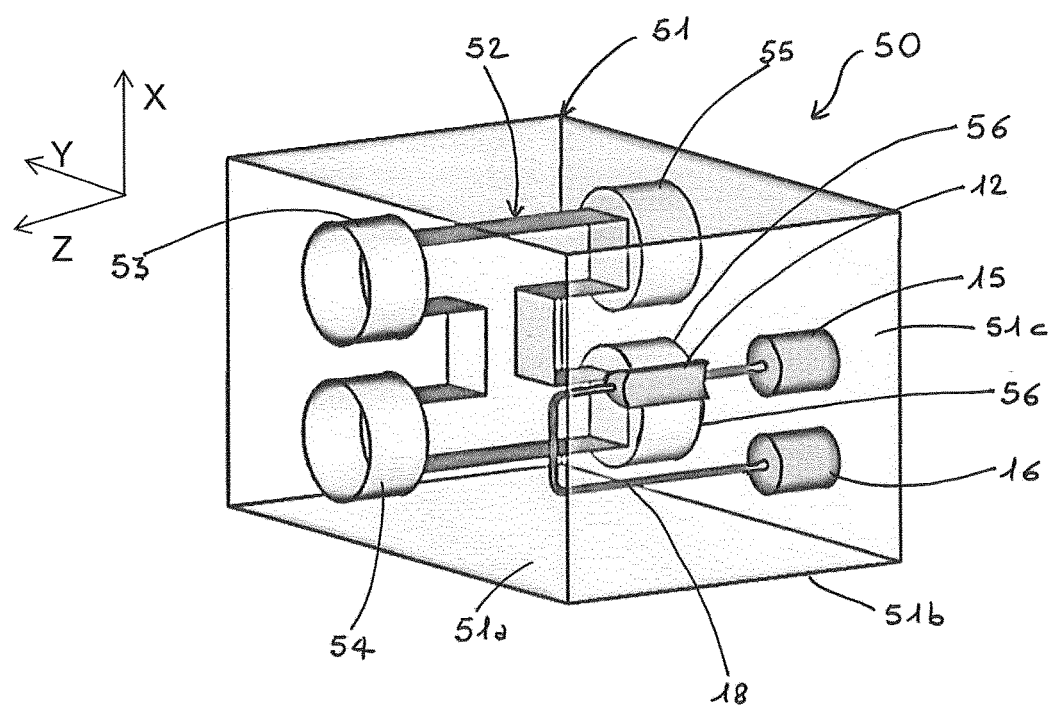
FIG. 4 is a perspective view of an integrated optofluidic device according to a third embodiment of the invention.

FIG. 4 is a perspective view of an integrated optofluidic device according to a third embodiment of the invention. Optofluidic lens and microfluidic arrangements in the substrate for loading and unloading the lens fluid correspond to those described with reference to the previous figures and are indicated with the same reference numerals. A main difference between the present embodiment and those shown in previous figures is the shape of the microfluidic channel. As explained more in detail in the following, the present embodiment allows to introduce in the microfluidic channel both a fluidic sample and a buffer fluidic stream, which can optimize the sample flow during measurement.

An optofluidic device 50 comprises a bulk substrate 51 made of a material transparent to light, preferably a glass substrate. An H-shaped microfluidic channel 52 is formed in substrate 51 as a hollow structure inside the bulk material of the substrate. The channel 52 comprises first and second inlet ports 54, 56 defining a respective opening on two opposite first and second surfaces 51a and 51c of the substrate. The microfluidic channel 52 further comprises a first outlet port 53 formed on the substrate first surface 51a and a second outlet port 55 formed on the substrate second surface 51c. In the embodiment of the figure, first inlet and outlet ports open on the same substrate surface, as well as second inlet and outlet ports open on the same substrate surface. In particular, first inlet port and second inlet port as well as first outlet port and second outlet port are access holes located on opposite surfaces of the substrate since this may simplify the channel structure and thus the channel fabrication. However, this configuration is not limitative and openings can be made on different surfaces of the substrate, for example by means of connecting channel sections, such as openings 53 and 54 can be formed in the YZ plane, on the surface 51c.

Figure 5:
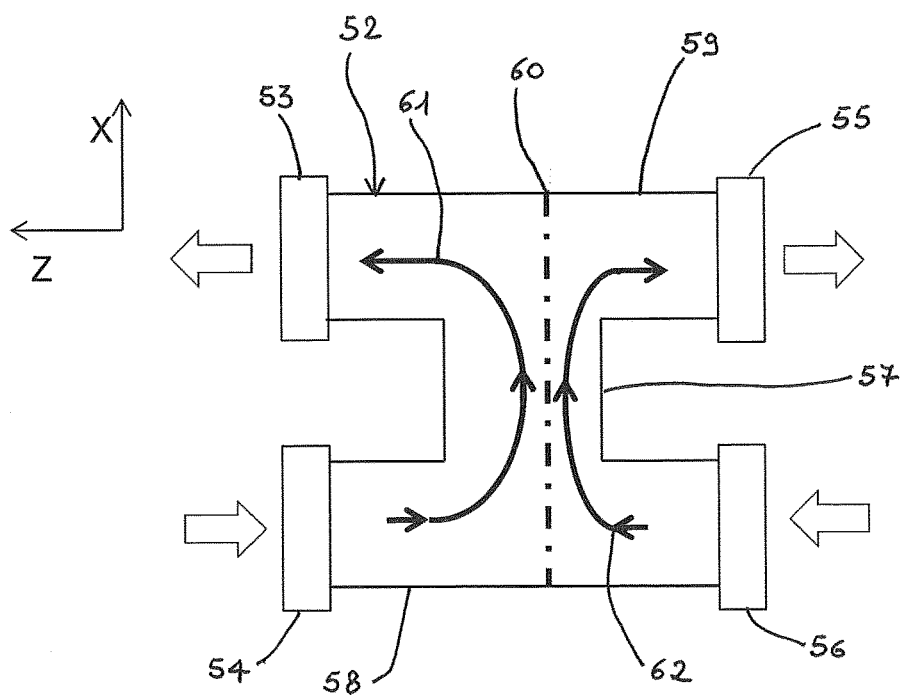
FIG. 5 shows flow paths in the microfluidic channel of FIG. 4, viewed in cross-section.

FIG. 5 is a cross-sectional view of the H-shaped channel 52 in an XZ plane (to improve clarity substrate 51 is not shown). The microfluidic channel 52 comprises two parallel channel branches, namely a lower branch 58 and an upper branch 59, and a connecting channel portion 57 transverse to the channel branches (opening into the lower and upper channel branches). Preferably, the connecting channel portion 57 is perpendicular to the upper and lower branches.

Preferably, upper channel branch 59 extends from the first outlet port 53 to the opposite second outlet port 55, whereas lower channel branch 58 extends from the first inlet port 54 to the opposite second inlet port 56. Preferably, connecting channel portion is a straight section of the channel.

The connecting channel portion is arranged in the substrate in a direction (X-axis) perpendicular to the main extension direction of the elongated lens cavity 12. Therefore, in use, the optofluidic device is arranged so that the connecting channel portion 57 extends in the detection direction (X axis) and the light sheet beam illuminates the connecting channel portion, after passing through the cylindrical lens, perpendicularly to the detection direction. The fluidic sample is inserted into first input port 54, while a buffer solution, namely a fluid without biological material to be analysed (i.e. pure buffer solution), is inserted into second inlet port 56. First input and output ports 54 and 53 are connected to a first flow circulating system (not shown) for flowing the fluidic sample from the first inlet port to the first outlet port. Second input and output ports 56, 55 are connected to a second flow circulating system (not shown) for flowing the buffer solution from the second inlet port 56 to the second outlet port 55. Because of the micrometric dimensions of the channel, at relatively low flow rates (controllable by an external pump system) the flow is laminar and the object is transported by the flow in a relatively predictable way, especially in the straight sections of the channel.

The two fluids flow from the respective inlet port to the connecting channel portion 57, where they merge without mixing because of the laminarity of the flows. FIG. 5 show flow paths 61 and 62 of the fluidic sample and of the buffer solution, respectively. The auxiliary flow of the buffer solution serves to create a virtual wall, indicated in FIG. 5 with dot-dashed line 60, for the flow of the fluidic sample.

Generally speaking, the position of the virtual wall or interface between the two fluids in the channel section depends on the input pressure of each fluid. If the pressure for injecting the fluidic sample is the same as the pressure for injecting the buffer solution, the interface would be located at about the middle of the channel. Controlling the input pressure allows a control of the interface position.

An advantage of this configuration of the microfluidic channel is that the flow of the buffer solution prevents the biological object travelling along the connecting channel portion 57 hitting a sidewall of the channel portion.

Figure 6:
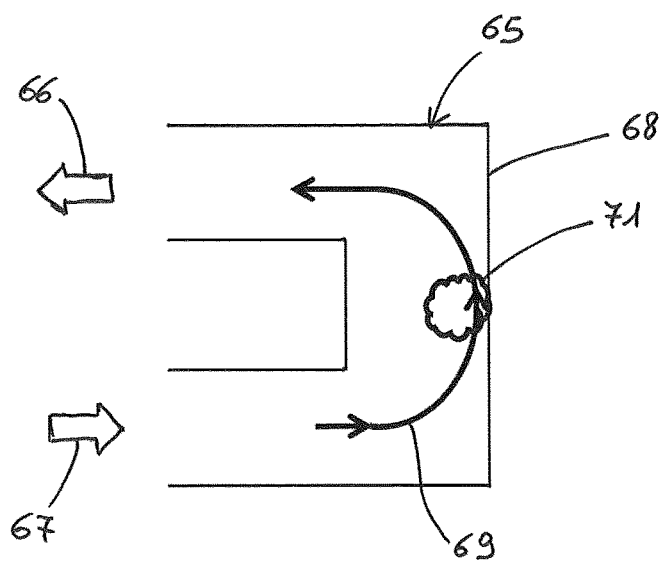
FIG. 6 shows a possible flow path of the fluidic sample in a C-shaped channel (viewed in cross-section).

FIG. 6 is a cross-sectional view of a C-shaped channel 65 with inlet opening 67 and outlet opening 66 for input and output of the fluidic sample. A flow path of the fluidic sample is shown by line 69 and the vertical intermediate channel portion is that illuminated by the light sheet. Under some circumstances, such as a high speed of the fluid or a large inertia of the object, an object 71 under analysis may hit sidewall 68 of the intermediate channel portion, the sidewall being opposite to the inlet port 67, due to inertia after the 90° turn of the moving object. This may induce rotation of the sample and perturb the images acquired during the object's motion. In the configuration of FIG. 5, the auxiliary flow of pure buffer avoids the object hitting the sidewall of the channel.

Figure 7:
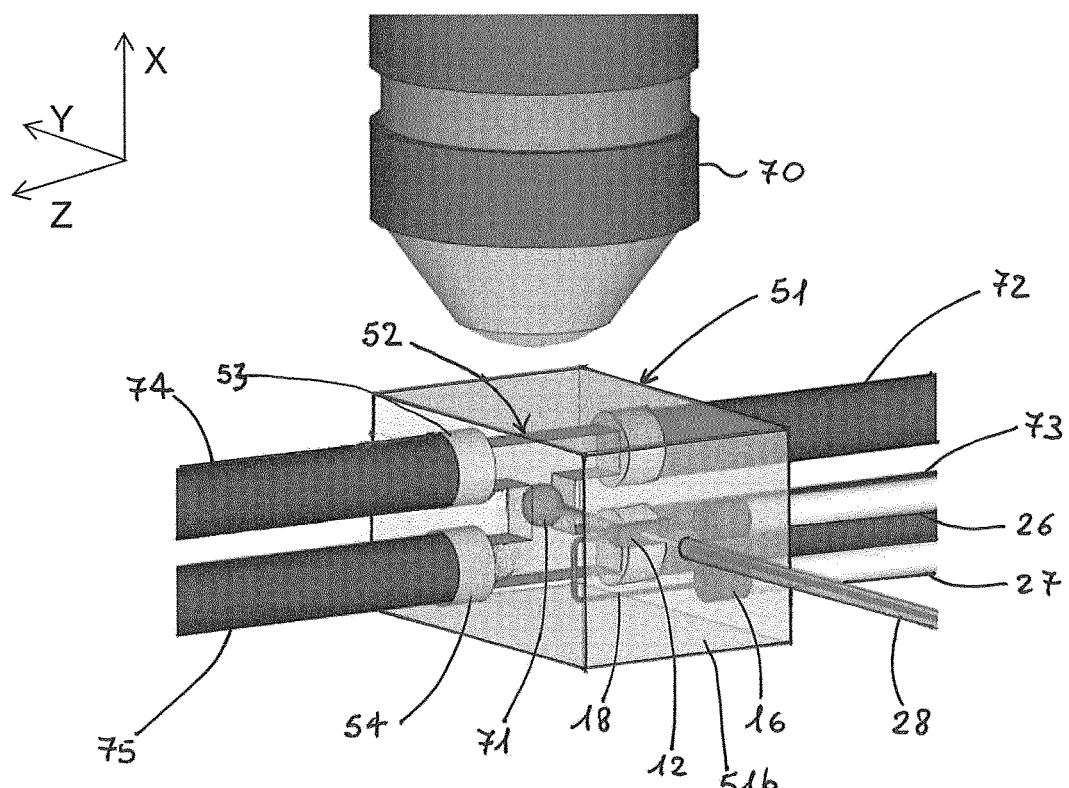
FIG. 7 is a perspective view of the optofluidic device of FIG. 4, further showing the tube connections and objective lens for detection of the fluorescence beam.

FIG. 7 is a perspective view of the optofluidic device of FIG. 4, showing the tube connections and the position of the microscope objective lens for detection of the fluorescence beam. The first inlet port 54 and the outlet port 53 are connected through tubes 74 and 75 to a first flow circulating system (not shown) for circulation of a fluidic sample containing objects to be analysed. The second inlet port 56 and the second outlet port 55 are connected through tubes 72 and 73 to a second flow circulating system (not shown) for circulation of a pure buffer solution. Tubes are only partly shown in the figure. Light beam transmitted by optical fibre 28 enters the substrate 51 through entry surface 51b, passes through cylindrical lens 12 (i.e. cavity filled by a transparent lens fluid) to be converted into a light sheet beam which passes through the fluidic sample in the connecting channel portion of microfluidic channel 52. In the embodiment shown in FIG. 7, a light beam enters the substrate from entry surface 51b along an irradiation direction (Y axis) perpendicular to the entry surface.

In some embodiments, access holes of inlet and outlet ports have a diameter larger than the cross-section of the branches of the microfluidic channel for flowing the sample so as to engage the outer surface of the external tubes. Preferably, the inner diameter of the tubes is equal or close to the cross-section of the channel so as to minimise possible flow turbulences due to a cross-section discontinuity.

In the embodiments described in the foregoing, the substrate of the optofluidic device has a shape of a rectangular or square parallelepiped. Surfaces of the substrate are thus perpendicular sidewalls. It is to be understood that other shapes of the bulk substrate can be envisaged as long as a correct geometry of the beam irradiation direction penetrating the sample flowing in a direction substantially perpendicular to the irradiation direction and to the light sheet beam is preserved.

Figure 8:
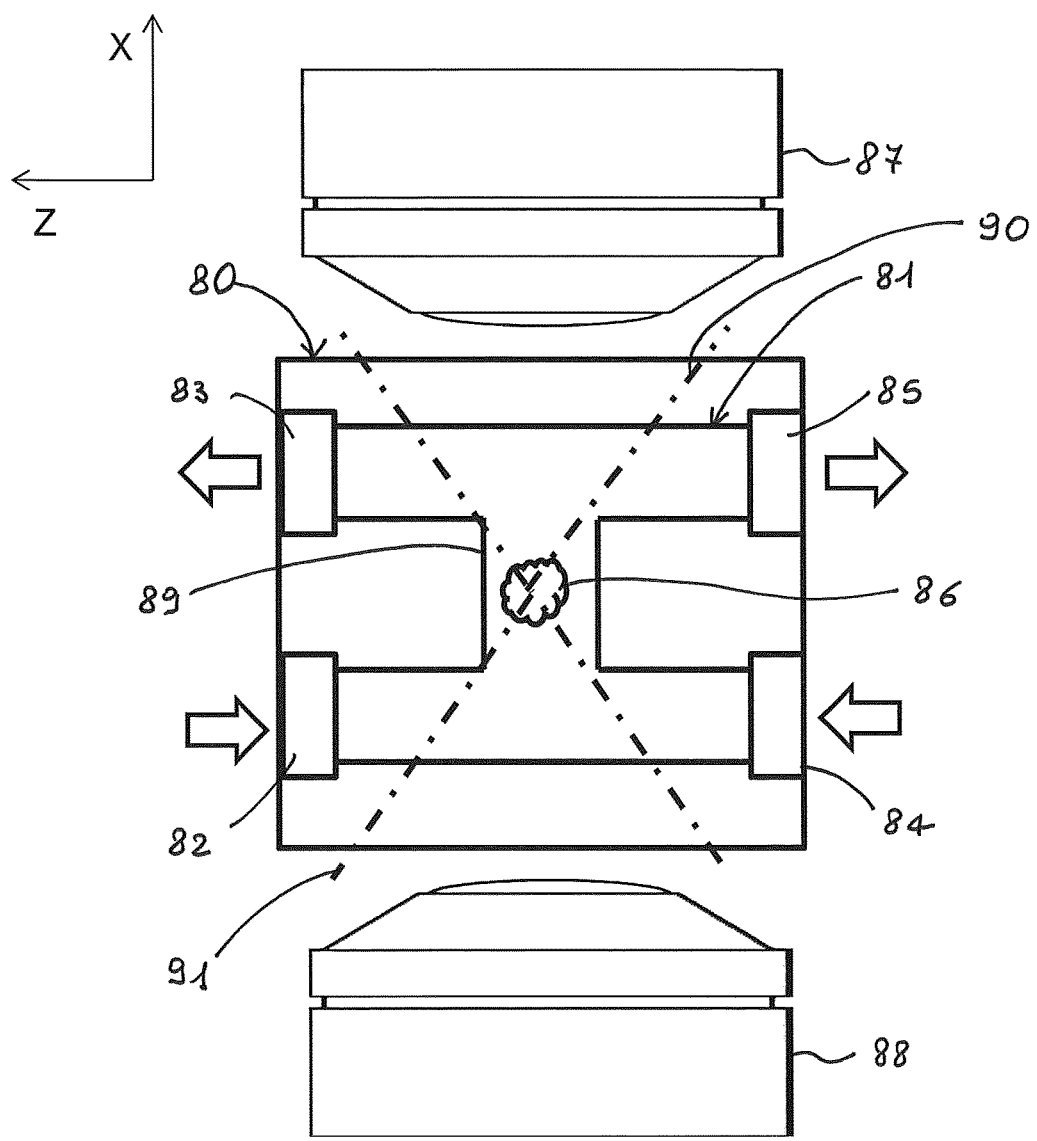
FIG. 8 is a cross-section of an optofluidic device with an H-shaped microfluidic channel showing a double-side detection arrangement, according to an embodiment of the present invention.

The C and H shapes of the microchannel allow to mount the optofluidic device in a microscope in such a way that two detection arrangements can be used for double-sided detection: two halves of an object of a fluidic sample can be acquired with two opposite microscope objective lenses and these two halves can be computationally combined to give an image with higher quality, particularly reducing the absorption and scattering effects in the sample. FIG. 8 is a cross-section of an optofluidic device comprising a substrate 80 in which an H-shaped microfluidic channel 81 is formed. The cross section is in a plane including the detection direction (X axis), across the microfluidic channel, and perpendicular to the irradiation direction. A fluidic sample flows in through inlet port 82 and exits from outlet port 83, whereas a buffer solution flows in through inlet port 84 and flows out from outlet port 85. Therefore, the fluidic sample, which contains an object 86, flows from bottom to top in the left portion of the channel since it is not mixed with the buffer solution (see FIG. 5). Arrows indicate the flow direction in and out of the two fluids. Two opposite microscope objective lenses 87 and 88, which are arranged so as to have their optical axis along the flow path of the sample (X axis), collect fluorescence light emitted from object 86 flowing bottom-up along the vertical connecting channel portion 89.

Objective lens 87 views the object from the top in the upper half of the channel 81, whereas objective lens 88 views the object from the bottom in the lower half of the channel, as schematically shown by acceptance cones for the objective lenses, indicated with dashed-dotted lines 90 and 91. Double-side detection is particularly advantageous in case of analysis of objects of relatively large size, e.g. larger than about 0.1 mm of diameter, such as spheroids, organoids, embryos or biopsies, which often give rise to significant light scattering.

The optofluidic device according to the present disclosure can be configured for a microscope that uses multiple-side illumination. Two (or more) cylindrical lenses can be fabricated in the bulk substrate of the device, preferably by means of FLM.

Figure 9:
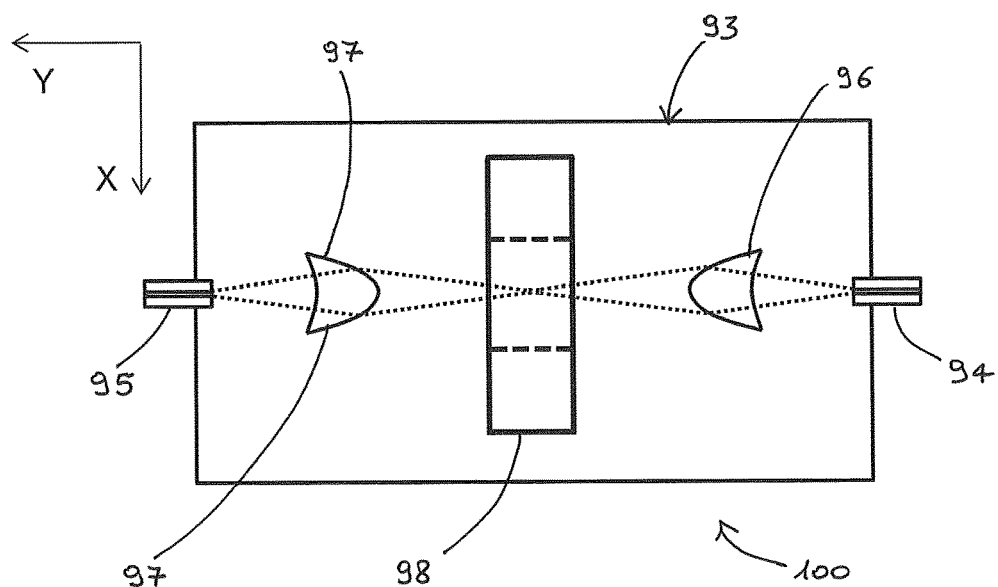
FIG. 9 is a cross-section of an optofluidic device suitable for multiple-side illumination, according to an embodiment of the present invention.

FIG. 9 is a cross-sectional view of an optofluidic device taken in a plane crossing the substrate (cutting the microfluidic channel and the lenses) and including the irradiation direction Y and the detection direction X. An optofluidic device 100 comprises a substrate 93 transparent to light, preferably made of glass, a microfluidic channel 98 formed in the substrate, a first lens cavity 96 for a first optofluidic cylindrical lens and a second lens cavity 97 for a second optofluidic cylindrical lens. First and second lens cavities are shown in cross-section in a plane perpendicular to their main extension axis. In the embodiment, cylindrical lenses are aspherical cylindrical lenses with a curved incidence wall having a concave shape with respect the incident light and a curved exit wall having a convex shape, always with respect to the incident light. Light beam is schematically indicated in the figures with a dotted line. A first beam enters the substrate from a first entry surface of the substrate, for example through a first optical fibre 94 and first beam enters the substrate from a second entry surface of the substrate, opposite to the first entry surface, for example through a second optical fibre 95. Microfluidic channel 98 comprises a channel portion (not visible in the figure) extending perpendicularly to the irradiation direction of the first and second beams. The main extension axis of the first and second cylindrical lenses is perpendicular to the channel portion. Preferably, the irradiation direction of first and second beam is the same. In some preferred embodiments, the irradiation direction is perpendicular to the respective entry surfaces of the substrate for the first and the second beam.

Multiple-side illumination is particularly advantageous in case of analysis of objects of relatively large size, e.g. larger than about 0.1 mm of diameter, which often exhibit significant light scattering or absorption.

Figure 10:
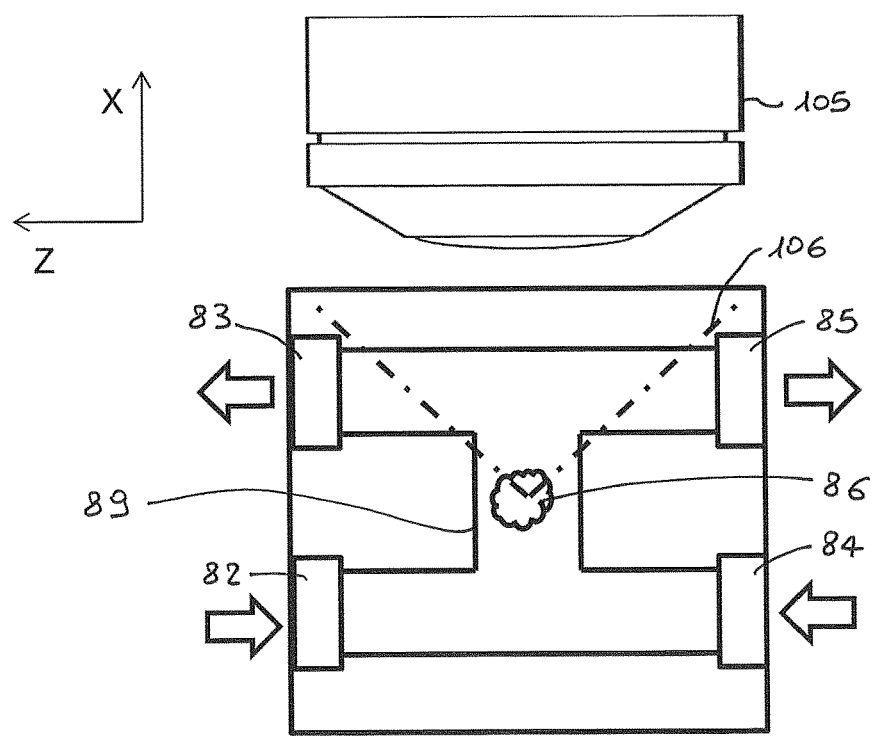
FIG. 10 is the cross-sectional view of the optofluidic device of FIG. 8 showing the light cone captured by an objective lens.

FIG. 10 shows the cross-sectional view of an optofluidic device of FIG. 8 with same referral numbers indicating same elements though in this embodiment there is single-side detection. The light that is captured by objective lens 105 (and recorded on an image sensor) can be considered as a cone, schematically indicated with dashed-dotted line 106, whose apex depends on the numerical aperture of the objective lens. When the numerical aperture is relatively high with respect to the channel cross-section, the detected image can be distorted by the microfluidic channel edges, such as corners between the upper channel branch and the vertical channel portion connecting the upper channel branch with the lower channel branch. In the embodiment shown in FIG. 10, the connecting channel portion is a straight section forming right angles with the upper and lower branches.

FIG. 11 shows a cross-sectional view of an optofluidic device, in plane XZ crossing H-shaped channel, according to a further embodiment of the invention. With respect to the embodiment of FIG. 10, the geometry of the H-channel and in particular the shape of its inside corners is modified. An optofluidic device 110 comprises a substrate 111 in which an H-shaped microfluidic channel 112 is formed, preferably by FLM. Channel 112 comprises inlet ports 113 and 114 and outlet ports 115 and 116. Arrows indicate the flow direction in and out of the two fluids. The microfluidic channel 112 further comprises upper and lower channel branches 122, 123, and a connecting channel portion 117 transverse to the channel branches opening into the upper and the lower channel branches. Preferably, upper channel branch 122 extends from the first outlet port 115 to the opposite second outlet port 116, whereas lower channel branch 123 extends from the first inlet port 113 to the opposite second inlet port 114. The connecting channel portion 117 extends along a main axis substantially perpendicular to the upper and lower branches. The connecting channel portion 117 has beveled joining portions 118, 119, 120, and 121 with the upper and lower branches 122 and 123 so as to define at each joining portion of the connecting channel portion with the upper or the lower branch two consecutive interior angles whose sum is 90°. A first interior angle is formed between the beveled joining portion and the main axis of the connecting portion, whereas a second interior angle is formed between the beveled joining portion and the main axis of the upper (lower) branch, wherein the main axis of the connecting portion is orthogonal to the main axes of the branches. In order to more clearly show the consecutive interior angles, an inset from FIG. 11, which is indicated with a dashed-lined square in FIG. 11, is enlarged in FIG. 11a. In FIG. 11a, first interior angle 124 of joining portion 121 is formed between the beveled joining portion and the main axis of the connecting portion 117, whereas second interior angle 125 of joining portion 121 is formed between the beveled joining portion and the main axis of the lower branch 123.

Figure 12:
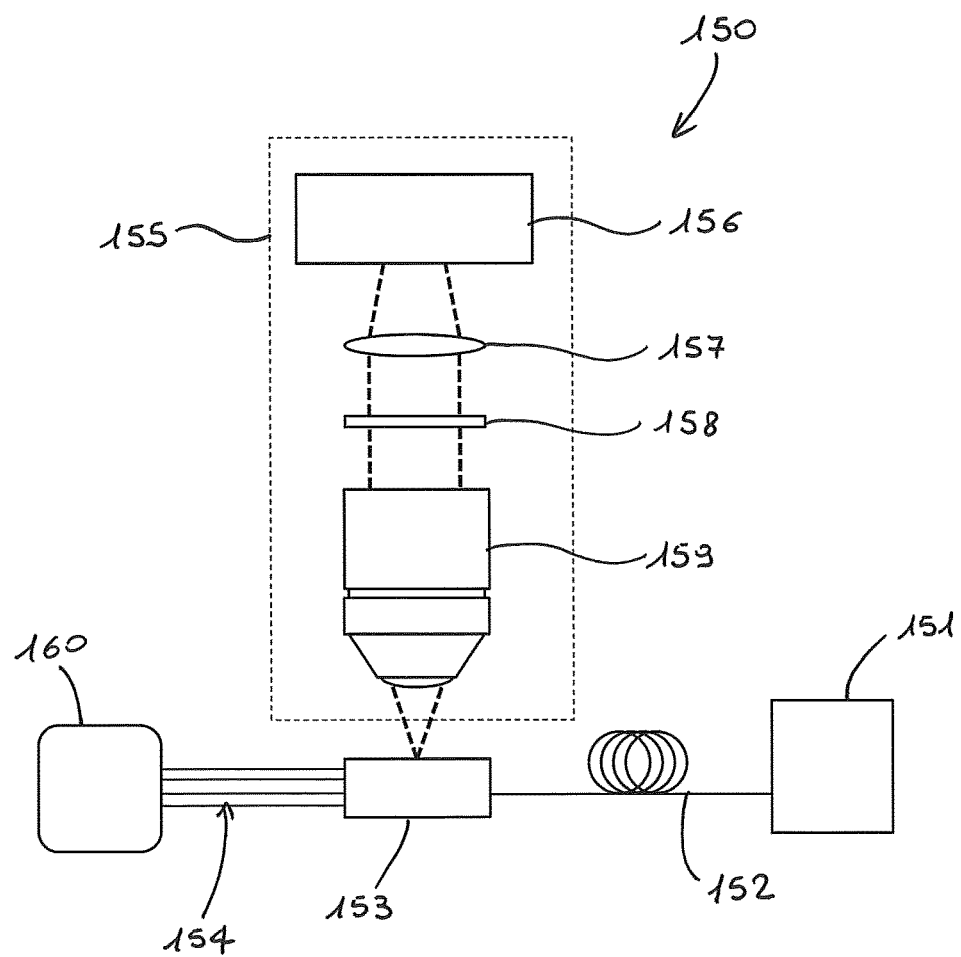
FIG. 12 is a schematic diagram of a light-sheet fluorescence microscope according to an embodiment of the invention.

FIG. 12 is a schematic diagram of a light-sheet fluorescence microscope (LSFM) comprising an optofluidic device consistent with the present disclosure, according to an embodiment of the invention. Preferably, the LSFM is a selective-plane illumination microscope (SPIM). A microscope 150 comprises the light source 151 configured to emit a light beam and an optical fibre 152 optically coupled to the light source and, at one its ends, to an optofluidic device 153 consistent with the present disclosure. For example, the optofluidic device can be of the type illustrates in FIGS. 1a-1b, 3a-3b, 4 and 11. No details of the optofluidic device are shown in FIG. 12.

The optofluidic device 153 comprises a bulk substrate made of a material transparent to the light emitted from the light source and comprising an incident surface for optical coupling with the optical fibre 112. A microfluidic channel is formed in the substrate, which is connected to a pump system 160 for circulation of a fluidic sample through two or more capillary tubes 154, made for example of polymeric material, such as PEEK (Polyaryletheretherketone). The device 153 comprises an optofluidic cylindrical lens embedded in the substrate and arranged in front of a channel portion of the microfluidic channel with respect to the incident beam transmitted by the optical fibre. As described in the foregoing, the optofluidic lens is constituted by a lens cavity formed in the substrate, which is filled by a fluid having a refractive index different from that of the material making the substrate. Flow circulation system for loading and unloading the lens fluid for the lens is not shown in the figure. In some embodiments the optical fibre is fixed to the incident surface of the device substrate at a position so as to emit light along an irradiation direction passing through the optofluidic lens and the channel portion of the microfluidic channel.

The cylindrical lens configured to convert the light beam entering the substrate of the device into a light sheet beam.

Preferably, the light source is a laser. Preferably, the light beam emitted by the light source is monochromatic. Preferably, the optical fibre is a single-mode optical fibre. In some embodiments, the light beam from the light source is in the visible or near-infrared wavelength region. The wavelength of the laser light is usually chosen to maximise the excitation efficiency of the biological material under study.

Preferably, the beam irradiation direction is perpendicular to the incident surface of the device substrate.

The microscope 150 further comprises a detection arrangement 155 configured to detect fluorescence light emitted from the sample. The detection arrangement 155 comprises a microscope objective lens 159 and a photodetector device 156 optically coupled to the microscope objective lens. The microscope objective lens 159 is arranged such that its optical axis is perpendicular to the irradiation direction. Preferably, the objective lens is a microscope objective lens with high numerical aperture. Preferably, the photodetector device 156 is a CMOS camera or a CCD camera.

Preferably, the detection arrangement comprises a fluorescence filter 158 arranged along the detection direction, so as to collect the light exiting the microscope objective lens 159. As per se generally known, the fluorescence filter blocks the excitation light and allows the fluorescence light to pass through, by exploiting the fact that the fluorescence light is emitted at a longer wavelength.

Preferably, the detection arrangement comprises also a tube lens 157 arranged along the detection direction between the objective lens and the photodetector device. As per se generally known, the tube lens is configured to focus the parallel light beam (i.e. imaged at infinity) exiting the objective lens at an intermediate image plane. The focused fluorescence light is then detected by the photodetector device. In an embodiment, the tube lens is an achromatic lens with focal length of 100 to 250 mm.

As customary in SPIM technique, the light sheet illuminates the object in a thin volume arranged around the front focal plane of the objective lens. The fluidic sample and in particular the object (e.g. a cell or embryo) to be analysed is placed at the intersection of the irradiation and detection axes. Light sheet thickness is usually chosen also in view of the size of the object to be imaged. Preferably, the light sheet has a uniform thickness across the full field of view of the camera so that single slices of the object are associated with a well-defined thickness. Microscope objective lens and tube lens create the image of the sample on the CCD (or CMOS) camera that acquires the fluorescence image. In the usual ways, the CCD camera 118 is connected to a processing unit (not shown), which controls the acquisition of images. The processing unit can be configured to acquire a plurality of images at given time intervals during the movement of the sample, and in particular of the object to be analysed contained in the fluidic sample. As the fluidic sample flows in the microfluidic channel along the detection axis, a plurality of 2D images are acquired. The presently disclosed device allows a continuous movement of the object through the light sheet plane, thereby providing the possibility to measure a plurality of objects in a fluidic sample, which flow one after the other along the illuminated channel portion. In an embodiment, scanning of the object is performed by flowing the sample at a constant speed through the light sheet.

Data processing by using image processing tools and algorithms, known per se, is carried out on the plurality of 2D slices for the construction of a 3D image of the measured object.

Example

An optofluidic device of the type shown in FIG. 4 was fabricated. The device was realized from a bulk substrate of fused silica by using femtosecond laser micromachining FLM. The technique was a two-step fabrication process: (1)

permanent material modification following nonlinear absorption of focused femtosecond laser pulses; (2) etching of the laser modified zone by a hydrofluoric acid (HF) solution. The laser irradiation enhances the etching rate by up to two orders of magnitude with respect to the pristine material, enabling the manufacturing of channels with arbitrary shape in the bulk glass substrate. The irradiation in step (1) was performed by focusing, through a 50×0.6 NA microscope objective, the second harmonic of a commercial femtosecond laser (femtoREGEN, HIGH-Q Laser) emitting pulses of 400 fs, 1040 nm wavelength and energy up to 23 µJ at 960 kHz repetition rate. Scan velocities and pulse energies were varied in relation to the depth of the irradiated structure with respect to the glass surface to compensate the spherical aberrations.

The geometry of the device was obtained by properly translating the substrate with respect to the laser beam with a commercial system of high-precision air-bearing translation stage (Fiberglide 3D, Aereotech), allowing the translation along the three dimensions.

The hollow structures forming the different elements of the device, i.e. the lens cavity, the lens loading channel and the microchannel network along with their respective access holes for connection with external tubes, were produced by irradiating the substrate with pulse energies of 270 nJ for the lens, 350 nJ for the access holes and 500 nJ for the microchannel. The translation speed of the sample with respect to the laser beam was 1 mm/s for the lens and 2 mm/s for all other hollow structures. The translation stage allowed two different irradiation directions: a longitudinal irradiation direction parallel to the laser beam propagation direction and a transverse irradiation direction orthogonal to the first irradiation direction. The first irradiation direction was employed for the formation of the lens cavity. For the definition of the channel for the lens cavity, irradiation was carried out in a direction parallel to the writing beam in order to reduce the roughness of the sidewalls of the channel to few nanometres. An aspherical profile of the cylindrical lens cavity was obtained by irradiating from the bottom to the top of the glass substrate 50 sections of the lens (separated in depth of 6 µm), each section having an optimized profile designed for reduction of spherical aberrations.

The transverse irradiation geometry was used to fabricate an H-shaped microchannel with square cross-section. In particular, a multi-scan irradiation approach was employed, in which contiguous straight lines were scanned (with a separation of 2 µm), thereby forming the lateral surface of a rectangular cross-section cylinder. For each channel branch of the H-shaped channel, six coaxial cylinders were irradiated (with dimensions of 40×30, 90×70, 180×150, 280×240, 380×330, 480×400 µm$^2$), so as to obtain the desired channel with a square cross-section of side of 500 µm after the etching step. Similarly, circularly-shaped access holes were obtained by irradiating seven coaxial circular helices with diameters equally spaced from 80 µm to 560 µm.

The total irradiation time for defining the surfaces of the hollow structures for the cylindrical lens and the microfluidic channel was approximately 2 hours. The substrate was then immersed in a HF solution to form the hollow structures.

The lens cavity was filled with a high refractive-index fluid, namely Cargille having refractive index n=1.56, larger than that of fused silica (n=1.46). The focal length of the cylindrical lens was 700 µm, the beam waist 12 µm and the confocal parameter 400 µm.

A commercial pressure driven pump system (Fluigent, MCFS Flex) was used to inject and control the flow of a fluidic sample and of a buffer solution in the device. The velocity of the flow of both the fluidic sample and of the buffer solution was controlled by unbalancing the pressure at the inlet and outlet ports separately for each stream. The buffer stream was used to prevent spheroids touching the sidewall of the connecting channel portion. This was achieved by balancing the sample and channel driving pressures the interface between the two streams can be moved so as to make the objects under study flow orthogonally with respect to the light sheet without touching the channel wall that might induce a rotation of the sample.

The optofluidic device was placed in a SPIM of the type shown in FIG. 12. A 532 nm laser (Uniphase) was coupled into a single-mode optical fibre to illuminate the device (c.a. 5 mW). A 20× NA 0.45 objective lens (CFI S Plan Fluor ELWD 20×, Nikon) with long working distance (6.6-8 mm) and a correction ring for glass up to 2 mm was used to image the sample. The correction ring reduced the aberrations caused by the presence of glass and liquid. The objective lens, in combination with a tube lens (MT-1 Mitutoyo) created an image on a photodetector device. An electron multiplied CCD camera (Andor, LucaR), running at 12 Hz, was used to image fluidic samples slowly passing through the light sheet, while a low cost CMOS Camera (GS3, Pointgrey), running at 87 Hz, was used for high-throughput imaging.

The invention claimed is:

1. An integrated optofluidic device for irradiating, along an irradiation direction, a fluidic sample containing an object to be analysed, the device comprising:
   a substrate comprising an entry surface and being made of a material apt to transmit a light beam incident through the entry surface along an irradiation direction;
   a microfluidic channel formed in the substrate and comprising a first flow inlet port for loading a fluidic sample therein, wherein the microfluidic channel comprises a channel portion intercepting the irradiation direction and extending in a longitudinal axis perpendicular to the irradiation direction, and a first flow outlet port for outputting the fluidic sample so as to define a flow path for the fluidic sample from the first inlet port to the first outlet port, the flow path being perpendicular to the irradiation direction in the channel portion of the microfluidic channel, and
   an elongated lens cavity for an optofluidic lens extending along a main extension axis transverse to the irradiation direction and defining a lens axis, wherein the lens cavity is formed in the substrate and is arranged in the substrate to intercept the irradiation direction between the entry surface and the microfluidic channel portion, the lens cavity being in fluid communication with a lens inlet port formed in the substrate, and wherein the lens axis extends perpendicularly both to the longitudinal axis of the channel portion and to the irradiation direction.

2. The device of claim 1, wherein the elongated lens cavity is configured so as to form a cylindrical lens when filled with a lens fluid of different refractive index from the substrate and it is delimited by a curved incidence wall extending along the lens axis and a curved exit wall opposite to the light incidence wall and extending along the lens axis.

3. The device of claim 2, wherein the incidence wall has a circular-arc cross section having a first radius and the exit wall has a circular-arc cross section having a second radius different from the first radius.

4. The device of claim 2, wherein the incidence wall has a circular-arc cross section and an aspherical exit wall so as to define a cavity for an aspherical cylindrical lens.

5. The device of claim 1, wherein the microfluidic channel is in fluid connection with a pump circulating system for creating a differential pressure between the first flow inlet port and the first flow outlet port thereby controlling the flow of a fluidic sample through the channel.

6. The device of claim 1, wherein the lens cavity is filled with a lens fluid transparent to the light beam so as to form a microfluidic optical lens.

7. The device of claim 6, wherein the substrate is made of a material of a first refractive index and the lens fluid has a second refractive index different from the first refractive index.

8. The device of claim 1, wherein the lens inlet port defines a first opening on a first surface of the substrate and the lens cavity is in fluid communication with a lens outlet port formed in the substrate for unloading the lens fluid and defining a second opening on the first substrate surface or on a second surface of the substrate.

9. The device of claim 1, wherein the first flow outlet port is for circulating a flow of the fluidic sample from the first flow inlet port through the microfluidic channel to the first outlet port and the first flow inlet port and the first outlet port of the microfluidic channel define a respective opening on a surface of the substrate and the microfluidic channel has a C-shape with the channel portion intercepting the irradiation direction being a straight intermediate portion of the channel extending perpendicularly to the irradiation direction so as to define a flow path perpendicular to the irradiation direction.

10. The device of claim 1, wherein the first flow outlet port is for circulating a flow of the fluidic sample from the first flow inlet port through the microfluidic channel to the first outlet port, the microfluidic channel has an L-shape and the microfluidic channel portion intercepting the irradiation direction is a straight portion of the L-shaped channel extending perpendicularly to the irradiation direction so as to define a flow path perpendicular to the irradiation direction.

11. The device of claim 1, further comprising a second flow inlet port and a second flow outlet port, wherein the microfluidic channel has an H-shape and comprises a lower channel branch, an upper channel branch extending in a direction substantially parallel to the lower channel branch and a connecting channel portion transverse to the upper and lower channel branches and opening into them, the connecting channel portion corresponding to the channel portion intercepting the irradiation direction, and the connecting channel portion extends along a main axis perpendicular to the irradiation direction.

12. The device of claim 11, wherein:

the first inlet port and the first outlet port define a respective opening on a respective surface of the substrate or on a substrate surface being the same for the first inlet port and the first outlet port for circulating a flow of the fluidic sample from the first flow inlet port to the first outlet port, the second inlet port and the second outlet port define a respective opening on a respective surface of the substrate or on a substrate surface being the same for the second inlet port and the second outlet port for circulating a buffer fluidic stream from the second flow inlet port to the second outlet port, so that the flow of the fluidic sample and the flow of the buffer fluidic stream merge in the connecting channel portion.

13. The device of claim 11, wherein the connecting channel portion has bevelled joining portions with both the upper and the lower branches so as to define at each joining portion of the connecting channel portion with the upper or the lower branch two consecutive interior angles whose sum is 90°.

14. A light-sheet fluorescence microscope comprising:

an integrated optofluidic device of claim 1;

a light source configured to emit a light beam;

an optical fibre optically coupled to the light source and optically coupled at one its ends to the entry surface of the substrate at a surface position such that to emit light along an irradiation direction passing through the lens cavity and the channel portion of the microfluidic channel;

a microscope objective lens arranged with its axis extending along a detection direction perpendicular to the irradiation direction and configured to collect fluorescence light emitted from an object in the fluidic sample flowing in the microfluidic channel portion along the detection direction, and a photodetector device optically coupled to the microscope objective lens for detecting the fluorescence light.

15. A method of imaging an object in a fluidic sample, comprising:

providing an integrated optofluidic device according to claim 1, wherein the substrate is made of a material of a first refractive index and an elongated lens cavity is configured so as to form a cylindrical lens when filled by a lens fluid;

loading a lens fluid into the lens cavity so as to form an optofluidic cylindrical lens, the lens fluid having a second refractive index different from the first refractive index;

loading a fluidic sample containing an object to be analyzed into the microfluidic channel by positioning the object in the channel portion;

entering a light beam from an entry surface of the substrate of the optofluidic device along an irradiation direction;

passing the light beam through the optofluidic lens thereby generating a light-sheet beam in a plane comprising the irradiation direction and then through the channel portion, and receiving fluorescence light emitted from the object by means of a microscope objective lens arranged along a detection direction perpendicular to the irradiation direction.

16. The method of claim 15, wherein receiving fluorescence light is carried out while flowing the fluidic sample through the light sheet beam along the channel portion so as to create a relative movement between the object and the light-sheet beam in a direction perpendicular to the light sheet.

17. The method of claim 16, further comprising, after receiving fluorescence light:

recording a plurality of images at given time intervals during the movement of the fluidic sample through the light sheet, and analyzing the plurality of images to determine a characteristic of the object.

18. The device of claim 1, wherein the substrate is a block of light transparent material.

\* \* \* \* \*